(12) United States Patent
Svendsen

(10) Patent No.: US 6,716,197 B2
(45) Date of Patent: Apr. 6, 2004

(54) NEEDLE RETRACTING MECHANISM, NEEDLE HOLDER AND HYPODERMIC SYRINGE

(75) Inventor: Terje Svendsen, Asker (NO)

(73) Assignee: Syringus AS, Oslo (NO)

( * ) Notice: Subject to any disclaimer, the term of this patent is extended or adjusted under 35 U.S.C. 154(b) by 101 days.

(21) Appl. No.: 10/149,386

(22) PCT Filed: Dec. 18, 2000

(86) PCT No.: PCT/NO00/00433
§ 371 (c)(1),
(2), (4) Date: Jun. 12, 2002

(87) PCT Pub. No.: WO01/47588
PCT Pub. Date: Jul. 5, 2001

(65) Prior Publication Data
US 2002/0183695 A1 Dec. 5, 2002

(30) Foreign Application Priority Data
Dec. 23, 1999 (NO) .................................. 19996459

(51) Int. Cl.$^7$ ............................ A61M 5/00; A61M 5/32
(52) U.S. Cl. ...................................... 604/192; 604/198
(58) Field of Search .......................... 604/93.01, 110, 604/181, 187, 192, 198, 231, 236, 237, 238, 240, 244, 264, 265, 905, 907; 128/919

(56) References Cited

U.S. PATENT DOCUMENTS

| | | | |
|---|---|---|---|
| 5,049,133 A | 9/1991 | Villen Pascual | |
| 5,122,118 A | 6/1992 | Haber et al. | |
| 5,188,614 A | 2/1993 | Hart | |
| 5,605,544 A * | 2/1997 | Tsao | 604/110 |
| 5,782,804 A * | 7/1998 | McMahon | 604/110 |
| 6,267,748 B1 * | 7/2001 | Gulliksen et al. | 604/110 |

FOREIGN PATENT DOCUMENTS

| | | |
|---|---|---|
| WO | WO 92/05818 | 4/1992 |
| WO | WO 94/19037 | 9/1994 |
| WO | WO 98/3061 | 7/1998 |

* cited by examiner

Primary Examiner—Brian L. Casler
Assistant Examiner—Mark K. Han
(74) Attorney, Agent, or Firm—Young & Thompson

(57) ABSTRACT

An automatic needle retracting mechanism (1) for a hypodermic syringe (2) comprises a body (3) which slidingly supports a needle (27). A retainer (9) for an actuator (8) and the needle (27) is kept in a retaining position by a spacer (11), which after some time in contact with an injectant loses its mechanical strength. A filing of the needle with an injectant causes a deformation of the spacer (11), a release of the actuator (8) and a retracting of the retainer (9) and needle (27) into a needle retraction chamber (4). The needle retracting mechanism may also include an inner sleeve (20) which is manually movable towards the retainer (9) for a manual release of the actuator (8). The needle retracting mechanism may be included in a needle holder (33) or integrated in a syringe (2').

19 Claims, 13 Drawing Sheets

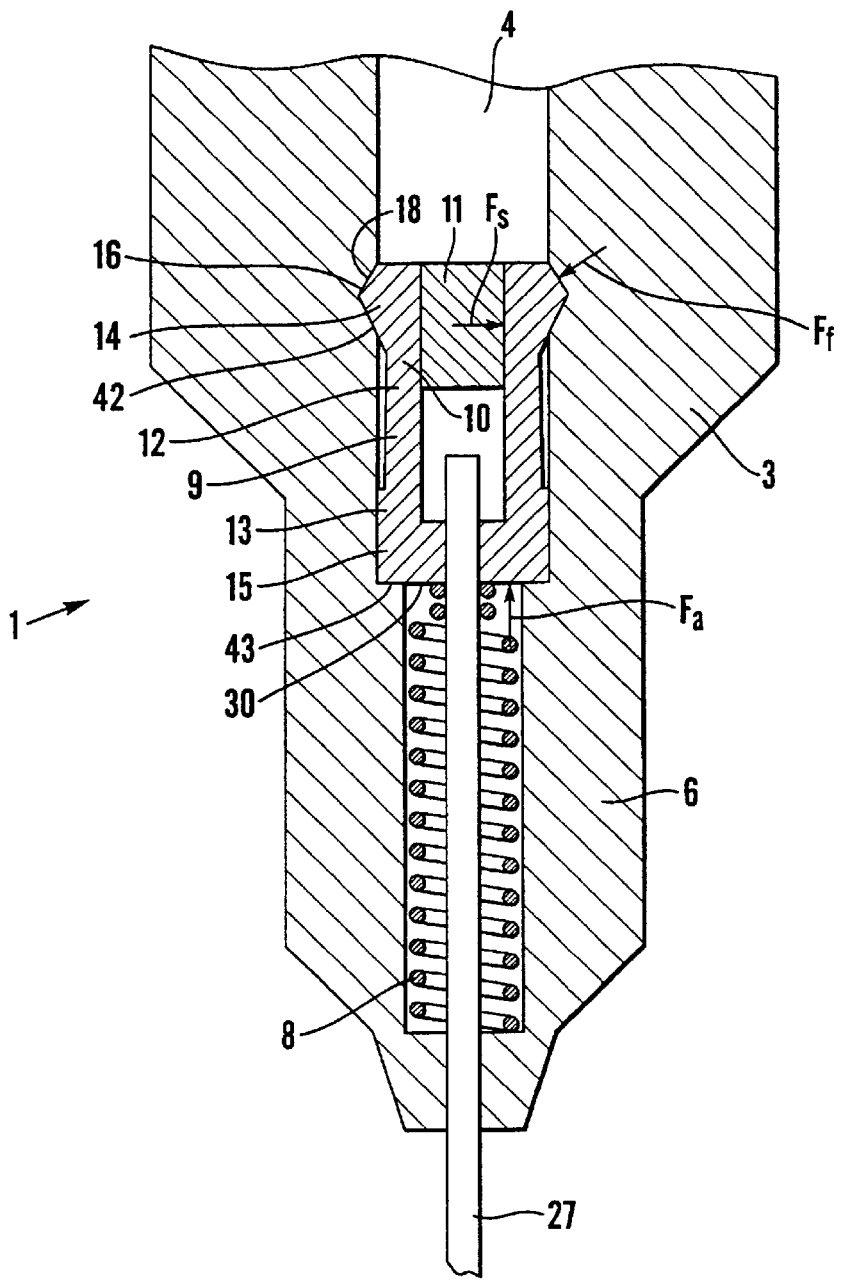
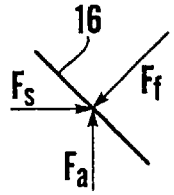
Fig.2a
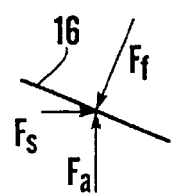
Fig.2b
Fig.2

NEEDLE RETRACTING MECHANISM, NEEDLE HOLDER AND HYPODERMIC SYRINGE

FIELD OF THE INVENTION

The invention relates to a needle retracting mechanism for a hypodermic syringe, comprising a body with a needle retraction chamber, which body in a first end is adapted to receive injectant from a syringe barrel and in a second end slidingly supports a needle which by means of a force from a pretensioned actuator is retractable into the needle retraction chamber, the actuator being releasable by response to the injectant.

The invention also relates to a needle holder for a hypodermic syringe, which needle holder comprises a needle retracting mechanism.

The invention also relates to a hypodermic syringe comprising a barrel and a plunger, which syringe comprises a needle retracting mechanism.

BACKGROUND OF THE INVENTION

Needles of used syringes constitutes a risk, both by themselves and as a source to contagion. Re-use of syringes constitutes a particular risk for contagion.

Most syringes are disposable syringes with a standardised fitting which can mate corresponding standardised fittings of syringe needles. This standardised fitting enables a wide range of combinations of various syringe sizes and needle sizes. A common standardised fitting is the Luer fitting.

Various safety syringes, in which the needle is retracted after use are known.

U.S. Pat. No. 5,122,118 describes an automatic needle retracting syringe in which a gelatine capsule retains a helical spring. Upon contact with the liquid injectant, the gelatine capsule weakens and allows the spring to retract the needle into the body of the syringe.

U.S. Pat. No. 5,049,133 describes a manual needle retracting syringe in which a spring which can retract the needle into the body of the syringe is releasable by moving the plunger to trigger a plurality of teeth-shaped hinges.

U.S. Pat. No. 5,188,614 describes a protective casing for use with a hypodermic syringe. A dual component foaming agent is disposed in the casing. When the components are mixed together they form an expanding and hardening plastic foam. Upon pressing the syringe into the casing subsequent to the ejection of fluid from the syringe, the foaming agents are activated and the expanding foam forces the syringe and syringe needle rearwardly within the casing, and encapsulates the used needle within the casing and foam.

WO-A-9 205 818 describes an automatic needle retracting syringe in which a spring which forces the needle into the plunger is released by pressing the plunger into the barrel after use.

WO 98/30261 describes a needle holder for use in combination with a syringe and a needle. The needle holder is provided with an expandable element and retention means for the expandable element. Contact between the expandable element and an injectant causes the expandable element to expand and retract the needle into the needle holder. The invention also relates to a syringe comprising the needle holder.

Prior art automatic needle retracting syringes which function by a response to the injectant, i.e. water, are generally encumbered with an unreliable and unpredictable release of the actuator.

Prior art manual needle retracting syringes are generally encumbered with the drawback that the force which is required to release the actuator is so large that using the safety syringe is felt cumbersome.

In some of the above mentioned safety syringes the needle and the retracting mechanism are integrated in the syringe barrel. There is therefore no possibility of combining variable syringe sizes with various needle sizes, which means that a greater number of syringe variants must be held in stock to satisfy all needs. Logistically this is a big problem.

A favourable material which respond to the injectant is alginate, which loses its mechanical strength and eventually dissolves in water. Alginate items are formed by extrusion or moulding. The resulting items are fragile and mechanically weak, which means that they easily deform or break. From a mechanical point of view, alginate is therefor not a preferable material.

SUMMARY OF THE INVENTION

The object of the invention is to provide an improved safety syringe in which the above problems are reduced or eliminated. Another object is to provide a safety syringe with both an automatic and a manual needle retracting mechanism. A further object is to provide an automatic needle retracting syringe in which alginate is suitable as material in the injectant responding item.

The objects are achieved by a needle retracting mechanism, a needle holder and a hypodermic syringe according to the preamble, which are characterized by the features of the claims.

In a first aspect the invention thus relates to a needle retracting mechanism for a hypodermic syringe, comprising a body with a needle retraction chamber, which body in a first end is adapted to receive injectant from a syringe barrel and in a second end slidingly supports a needle which by means of a force from a pretensioned actuator is retractable into the needle retraction chamber. The needle retraction chamber is provided with a funnel-shaped entrance opening, which widens out towards a retainer for the actuator and needle. The retainer comprises a compressible portion which in a retaining position is bigger than the entrance opening and abuts funnel-shaped sides of the entrance opening, and in a compressed release position is smaller than the entrance opening, and thus can enter the entrance opening. The pretensioned actuator forces the retainer into the funnel-shaped entrance opening, i.e. the actuator forces the compressible portion towards the release position. The compressible portion is, however, kept in the retaining position by a spacer. The spacer is made from a material which after some time in contact with the injectant loses its mechanical strength.

In storage no injectant is present, and the spacer maintains its mechanical strength and shape, which means that the compressible portion of the retainer is maintained in its retaining position.

When the syringe is filled with an injectant, a contact between the spacer and the injectant takes place, which after some time causes the spacer to lose its mechanical strength. The spacer then no longer maintain the compressible portion of the retainer in its retaining position, and the actuator therefore forces the compressible portion into the release position, and into the entrance opening. The width of the needle is smaller than the entrance opening, and both the needle and the retainer is forced through the entrance opening and into the needle retraction chamber. It is thus provided an automatic release of the needle retraction.

Preferably the compressible portion of the retainer comprises elastic arms which in first ends are integral with a base portion of the retainer and in second ends are moveable between the retaining position and the release position. The second ends of the elastic arms preferably have oblique end faces, corresponding to the funnel-shaped sides of the entrance opening. Further the elastic arms preferably have mountings for the spacer.

When the compressible portion of the retainer is in the retaining position and keeps the actuator in place, a force from the funnels-shaped sides of the entrance opening attacks the compressible portion of the retainer. This force is counteracted by a force from the compressible portion of the retainer, which force is a resultant of the force from the actuator and a force between the compressible portion and the spacer. Assuming no friction, the forces which act between the funnel-shaped entrance opening and the compressible portion of the retainer are perpendicular to the funnel-shaped sides. Depending on the angle of the funnel-shaped sides, which is a matter of design choice, the force between the compressible portion and the spacer can be made much smaller than the force from the actuator.

Practically there will be a friction between the funnel-shaped sides of the entrance opening and the compressible portion of the retainer, but still the force between the compressible portion and the spacer can be made much smaller than the force from the actuator by selecting the angle of the funnel-shaped sides.

For practical purposes, the injectant is an aqueous solution. Alginate has favourable characteristics with respect to dissolving in water, and is therefore well suited as a material for the spacer. As mentioned, alginate is, however, mechanically weak. In prior art automatic needle retracting mechanisms the item which loses its mechanical strength upon contact with the injectant is attacked by the force from the actuator, and alginate has thus not been suitable. In the inventive automatic needle retracting mechanism, the force which attacks the item which loses its mechanical strength upon contact with the injectant, i.e. the force between the compressible portion and the spacer, can be made much smaller than the force from the actuator by selecting the angle of the funnel-shaped sides, as discussed above. The invention thus enables the use of alginate in this item. The dissolving of alginate is reliable and predictable, and it is thereby provided a reliable and predictable automatic needle retraction.

In a preferred embodiment the needle retracting mechanism also comprises an inner sleeve which forms the needle retraction chamber and in an end proximal to the retainer is provided with the funnel-shaped entrance opening. The sleeve is movable relative to the body, towards the retainer. Further this embodiment includes an abutment which prevents the retainer from moving towards the second end of the body.

This embodiment enables a manual needle retraction by moving the sleeve towards the retainer. The retainer is kept in place by the abutment, and the funnel-shaped sides of the entrance opening, i.e. the end of the sleeve, presses the compressible portion of the retainer towards the release position. The spacer is mechanically weak, and is deformed or broken, whereupon the funnel-shaped sides of the entrance opening and/or the actuator forces the compressible portion into the release position and into the entrance opening. The actuator then forces the retainer and needle into the needle retraction chamber.

This embodiment thus provides a needle retracting mechanism which is both automatically and manually releasable. The manual release may be used if a quick retraction of the needle is preferred, or if the automatic release for some reason fails. The force which is required to deform or break the alginate during the manual release is moderate, as the alginate is weakened by the injectant. Thus the required force to produce a manual needle retraction is also moderate.

In a second aspect the invention relates to a needle holder for a hypodermic syringe, comprising a needle retracting mechanism according to the invention, as discussed above.

A first embodiment of the needle holder comprises the automatic needle retracting mechanism only, i.e. the first end of the body is adapted to match an outlet from a syringe barrel, and there is no sleeve.

A second embodiment of the needle holder comprises both the automatic needle retracting mechanism and the manual needle retracting mechanism, i.e. the needle holder also comprises a sleeve. The end of the sleeve distal to the retainer is adapted to match an outlet from a syringe barrel. The body of the holder is slideable on the sleeve, from an operating position in which the compressible portion of the retainer is in the retaining position and the needle is operable, to a retracted position in which the sleeve is moved towards the retainer, causing the release of the actuator and the retraction of the needle.

In a preferred embodiment of the needle holder, the body and the sleeve are relatively movable to a position in which the retainer is located in the first end of the body, the actuator is relieved and the needle is drawn into the body. This position is designated the extended position. Prior to using the syringe, the body is slid to the operating position, in which the retainer is located in the second end of the body, the actuator is pretensioned and the needle is operable.

In a third aspect the invention relates to a hypodermic syringe comprising a barrel and a plunger, with a needle retracting mechanism according to the invention, as discussed above.

A first embodiment of the hypodermic syringe comprises the automatic needle retracting mechanism only, in which the first end of the body forms an extension of the barrel.

A second embodiment of the hypodermic syringe comprises both the automatic and the manual needle retracting mechanism, i.e. the hypodermic syringe also comprises a sleeve. The first end of the body forms an extension of the barrel, and the end of the sleeve distal to the retainer forms an abutment for the plunger when the plunger is close to the bottom of the barrel, causing a further movement of the plunger into the barrel to force the sleeve towards the retainer, causing the release of the actuator and the retraction of the needle.

BRIEF DESCRIPTION OF THE DRAWINGS

The invention will now be explained in closer detail with reference to the enclosed drawings, in which:

FIG. 2 illustrates the automatic needle retracting mechanism in FIG. 1 in a larger scale, FIGS. 2a and b illustrate forces in the needle retracting mechanism.

DETAILED DESCRIPTION OF THE INVENTION

Figure 1:
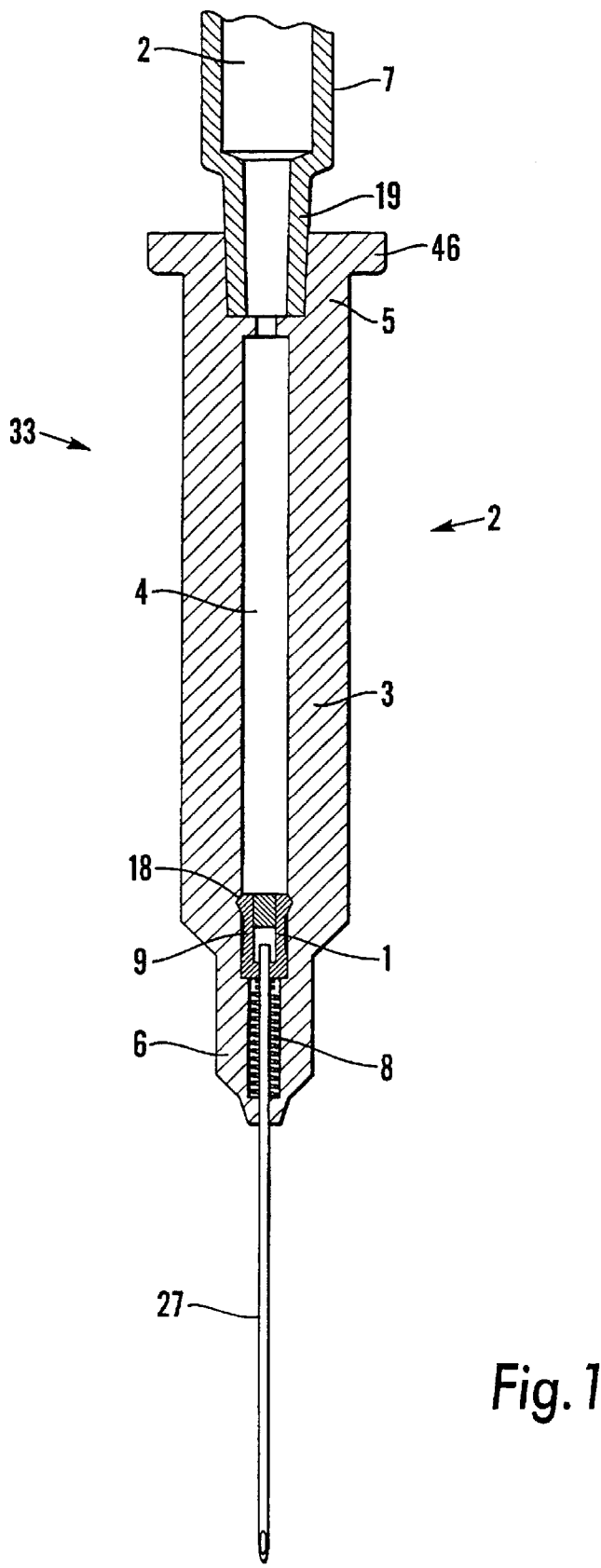
FIG. 1 illustrates a needle holder with an automatic needle retracting mechanism according to the invention, with a retainer in a retaining position.

FIG. 1 illustrates a needle holder 33 with an automatic needle retracting mechanism 1 according to the invention. The needle retracting mechanism comprises a body 3 which in a first end 5 is fitted to the outlet 19 of a syringe barrel 7 of a disposable hypodermic syringe 2, in order to receive injectant from the syringe barrel 7 during use. The syringe 2 is of a type which is available in various sizes, with the outlet 19 designed as a standard Luer fitting. The needle holder 33 may thus be used for a number of various standard syringes.

A second end 6 of the body 3 slidingly supports a needle 27, which by means of a force from a pretensioned actuator 8 is retractable into a needle retraction chamber 4 in the body 3. The actuator 8, which is a helical spring, is retained in a pretensioned position by a retainer 9.

FIG. 2 illustrates the automatic needle retracting mechanism in FIG. 1 in a larger scale. The retainer 9 comprises a base portion 15 and a compressible portion 10. The retainer base portion 15 comprises an abutting portion 30 for the actuator 8. The abutting portion 30 is a flat side of the retainer 9 which faces the actuator 8, and is prevented from moving towards the actuator 8 by a nose 43 in the first end 6 of the body 3.

Figure 3:
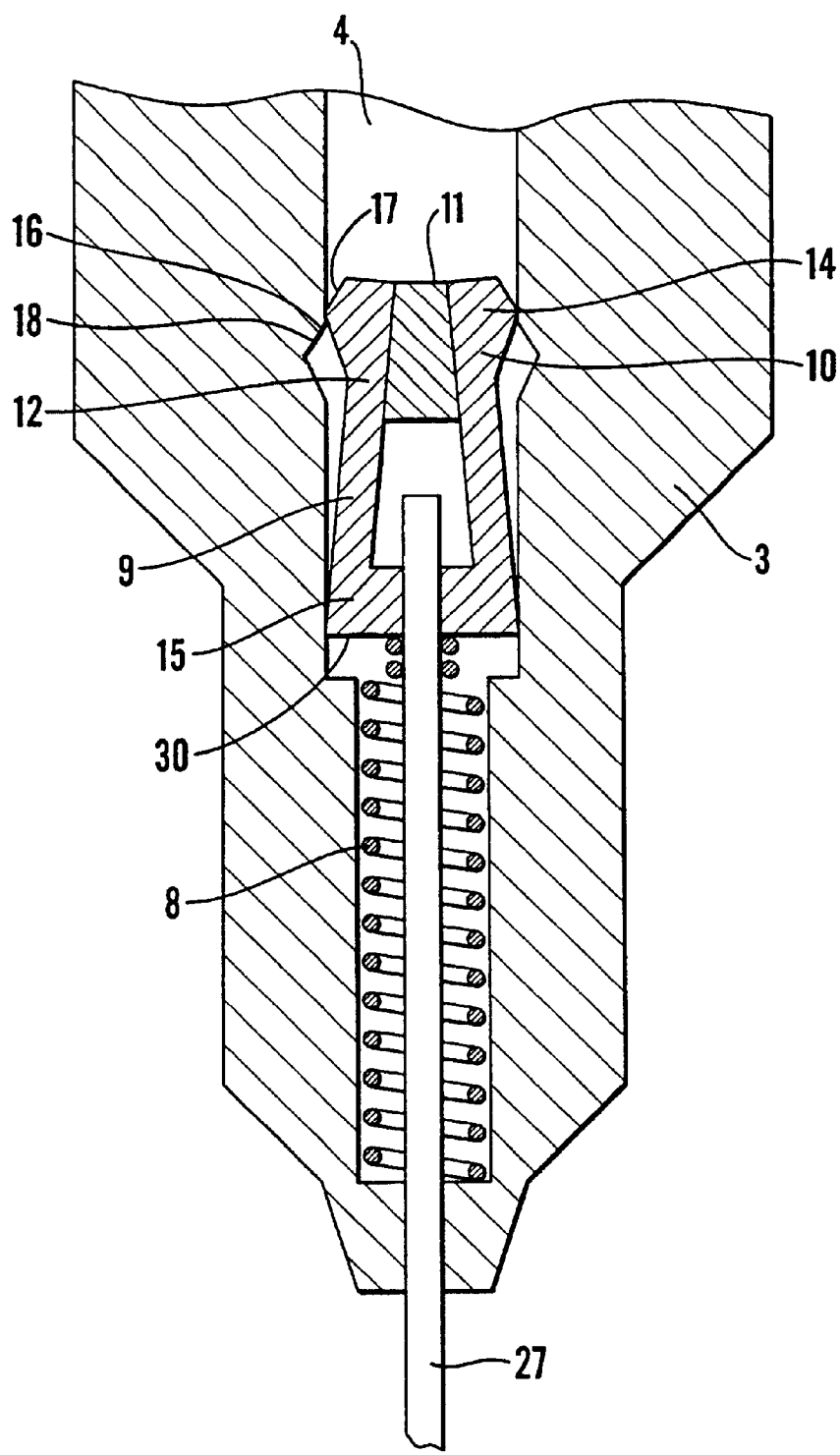
FIG. 3 illustrates the automatic needle retracting mechanism in FIG. 1 with the retainer in a release position.

In the illustrated embodiment, the compressible portion 10 comprises elastic arms 12 which in first ends 13 are integral with the base portion 15, and in second ends 14 are moveable between a retaining position which is illustrated in FIGS. 1 and 2, and a release position which is illustrated in FIG. 3, and which will be discussed later.

The needle retraction chamber 4 has a funnel-shaped entrance opening 18, which is formed by funnel-shaped sides 16. Together with adjoining, oblique holding sides 42, the funnel-shaped sides 16 keep the second ends 14 of the elastic arms 12 in place. The holding sides 42 are favourable, however, they are not essential for the invention.

The actuator 8 forces the retainer 9 towards the funnel-shaped entrance opening 18, causing the funnel-shaped sides 16 to compress the compressible portion 10, i.e. the second ends 14 of the elastic arms are pressed together. The second ends 14 of the elastic arms are, however, kept in the retaining position by a spacer 11. In the retaining position, the second ends 14 of the elastic arms 12 are bigger than the entrance opening 18, and the retainer 9 is prevented from entering the needle retraction chamber 4.

The spacer 11 is made from a material which after some time in contact with the injectant loses its mechanical strength.

In FIG. 3, the syringe has been filled with an injectant, and the spacer 11 has lost its mechanical strength. The force from the actuator has caused the funnel-shaped sides 16 to compress the compressible portion 10, i.e. the second ends 14 of the elastic arms 12 are forced together, into the release position, and the spacer is deformed.

In the compressed release position, the second ends 14 of the elastic arms 12 are smaller than the entrance opening 18, and the retainer 9 is forced into the entrance opening 18 by the actuator 8. The needle 27, which has a width which is smaller than the entrance opening 18, is fixed to the base portion 15 of the retainer 9, and the needle 27 therefore enters the entrance opening together with the retainer 9. Both the retainer 9 and the needle 27 is thereby retracted into the needle retraction chamber 4, and an automatic needle retraction thus takes place.

The second ends 14 of the elastic arms 12 have oblique end faces 17, corresponding to the funnel-shaped sides 16 of the entrance opening 18, in order to facilitate the entering of the retainer 9 into the entrance opening 18.

Reference is again made to FIG. 2. When the second ends 14 of the elastic arms 12 are in the retaining position and keep the actuator 8 in place, each elastic arm 12 is attacked by a force from the corresponding funnels-shaped side 16. This force is counteracted by a force from the second end 14 of the elastic arm, which force essentially is a resultant of the force from the actuator 8 and a force between the elastic arm 12 and the spacer 11. Assuming no friction, the forces which act between the funnel-shaped sides 16 and the second end 14 of the elastic arm 12 are perpendicular to the funnel-shaped sides 16. Depending on the angle of the funnel-shaped sides 16, which is a matter of design choice, the force between the elastic arm 12 and the spacer 11 can be made much smaller than the force from the actuator 8.

This is illustrated in FIGS. 2, 2a and 2b, in which arrow $F_f$ is the force from the funnel-shaped side 16, arrow $F_s$ is the force from the spacer 11 on the elastic arm 12, and arrow $F_a$ is the force from the actuator. Assuming two arms, $F_a$ is the half of the total force from the actuator 8. According to the laws of mechanics, and neglecting other forces, $F_f$, $F_s$ and $F_a$ must be in equilibrium.

FIG. 2a illustrates the forces when the funnel-shaped side 16 have the angle which is illustrated in FIG. 2, while FIG. 2b illustrates the forces with a flatter funnel-shaped side 16. The forces are illustrated as vectors, i.e. the lengths of the arrows correspond to the magnitudes of the forces. It can be seen that the flatter funnel-shaped side 16 has made $F_S$ smaller.

Practically there will be a friction between the funnel-shaped sides 16 and the elastic arms 12, but still the forces between the elastic arms 12 and the spacer 11 can be made much smaller than the force from the actuator 8 by selecting the angle of the funnel-shaped sides 16.

For practical purposes, the injectant is an aqueous solution. Alginate has favourable characteristics with respect to dissolving in water, and is therefore well suited as a material for the spacer 11. As mentioned, alginate is, however, mechanically weak. In prior art automatic needle retracting mechanisms the item which loses its mechanical strength upon contact with the injectant is attacked by the force from the actuator, and alginate has been too weak to be used in this item. In the inventive automatic needle retracting mechanism, the force which attack the item which loses its mechanical strength upon contact with the injectant, i.e. the force between the elastic arms 12 and the spacer 11, can be made much smaller than the force from the actuator 8, and the invention thus enables the use of alginate in this item. The dissolving of alginate is reliable and predictable, and it is thereby provided a reliable and predictable automatic needle retracting mechanism.

Figure 4:
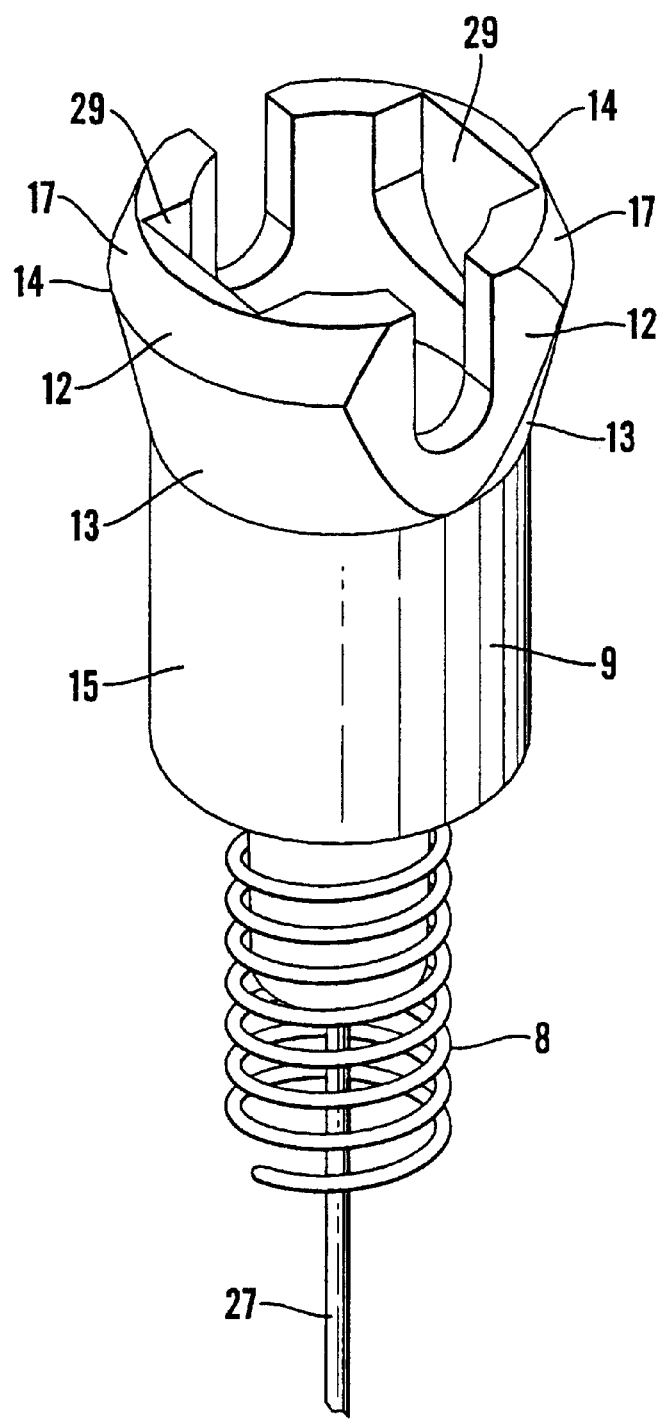
FIG. 4 illustrates a retainer according to the invention.

FIG. 4 illustrates a retainer 9 according to the invention, which differs slightly from the retainer in FIGS. 1–3. The retainer in FIG. 4 has two elastic arms 12, which in first ends 13 are integral with a base portion 15. The second ends 14 of the elastic arms 12 have mountings 29 for the spacer 11. The spacer, which will have the form of a bolt, and which will extend between the two mountings 29, is not illustrated.

Figure 5:
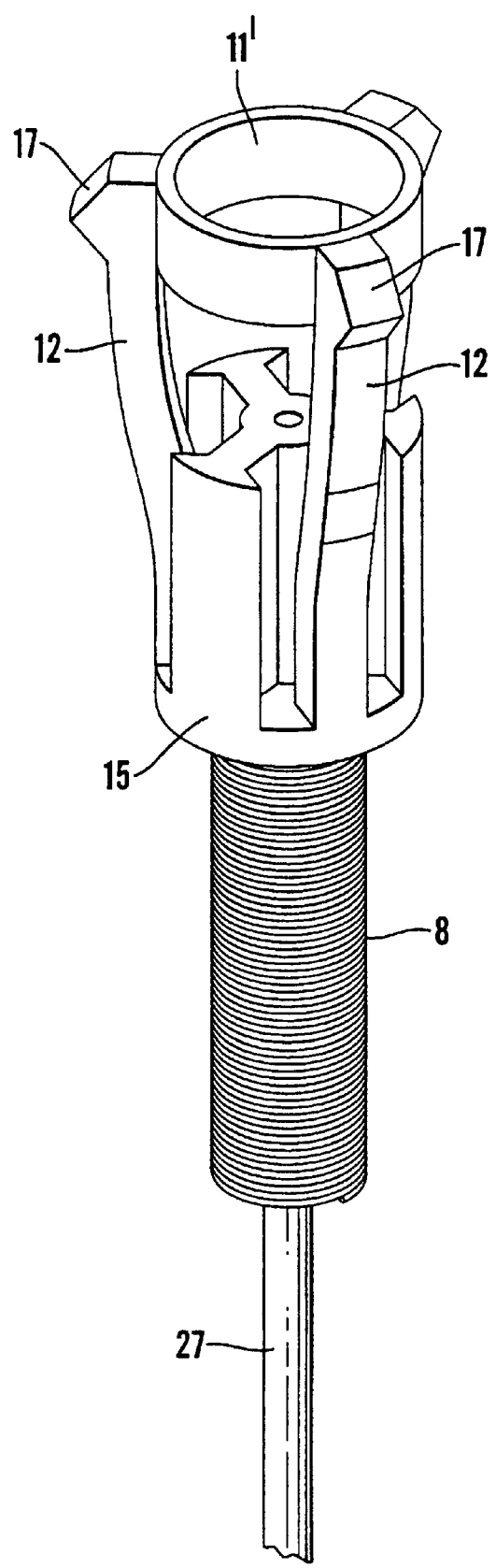
FIG. 5 illustrates another retainer according to the invention.

FIG. 5 illustrates another retainer 9 according to the invention. This retainer has three arms 12 and a spacer formed by a ring 11' which is mounted between the arms 12.

In other respects the retainers in FIGS. 4 and 5 correspond to the retainer in FIGS. 1–3.

Several retainer and spacer designs are conceivable. It is, however, required that the retainer and spacer do not prevent the injectant from flowing to the inlet of the needle. This requirement is met in all the illustrated retainers and spacers.

As mentioned, the spacer 11 is preferably made from alginate. Alternatively the spacer can be made from a water soluble biopolymer, e.g. chitosan, starch and modified starches, hyaluronic acid, guar, xanthan, cellulose acetate and other cellulose derivative or synthetic polymers e.g. polyvinyl alcohol, polyacrylic acid, polyacrylamide, polyesters and polyamines.

Figure 6:
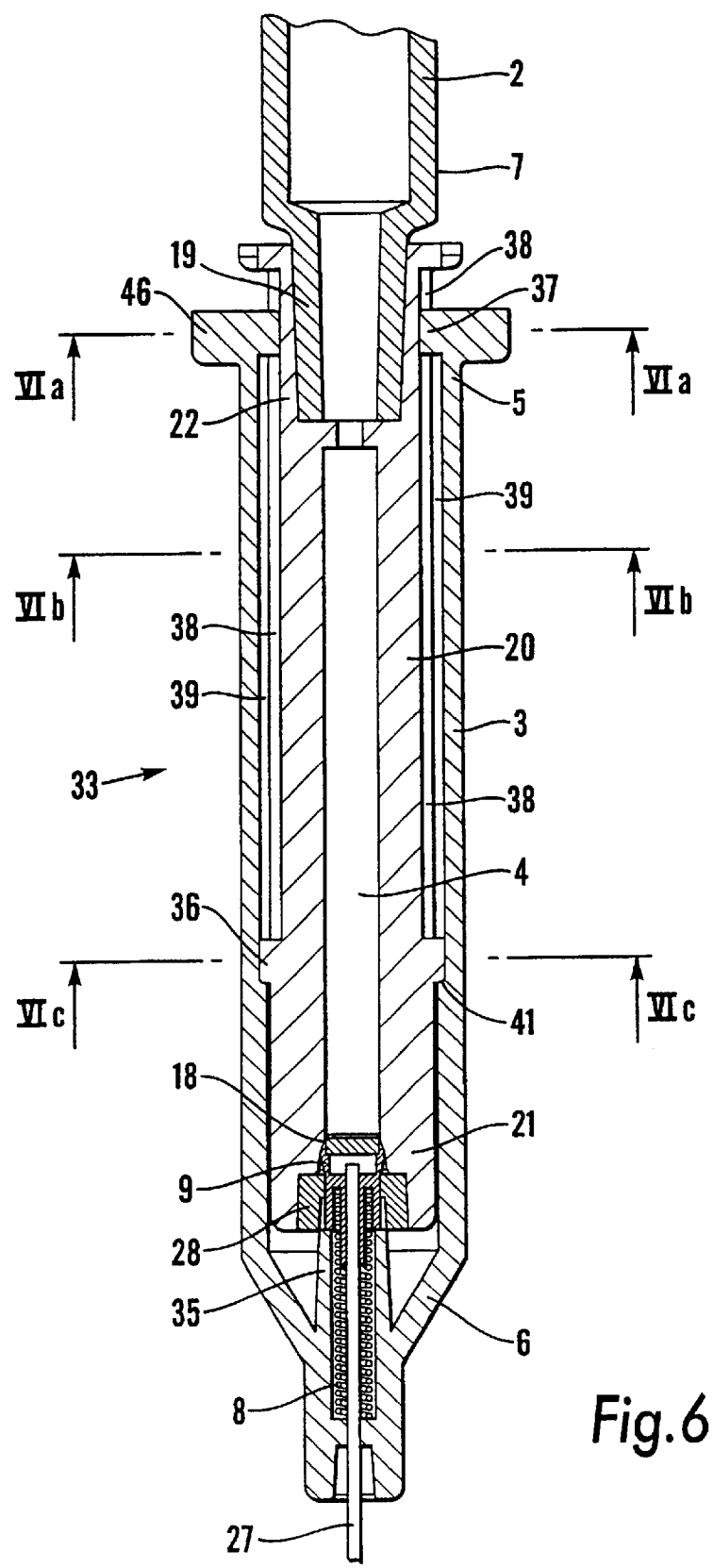
FIG. 6 illustrates a needle holder with an automatic and a manual needle retracting mechanism according to the invention, with the retainer in a retaining position.

FIG. 6 illustrates a needle holder 33 with an automatic needle retracting mechanism, in which the compressible portion is in a retaining position. Further the needle retracting mechanism in FIG. 6 also has the possibility of a manual release.

The needle holder in FIG. 6 has an inner sleeve 20 which forms the needle retraction chamber 4, and which in an end 21 proximal to the retainer 9 is provided with the funnel-shaped entrance opening 18. The end 22 of the sleeve 20 distal to the retainer 9 is adapted to match an outlet 19 from a syringe barrel 7. The syringe 2 is of a type which is available in various sizes, with the outlet 19 designed as a standard Luer fitting. The needle holder in FIG. 6 may thus be used for a number of various standard syringes.

Figure 7:
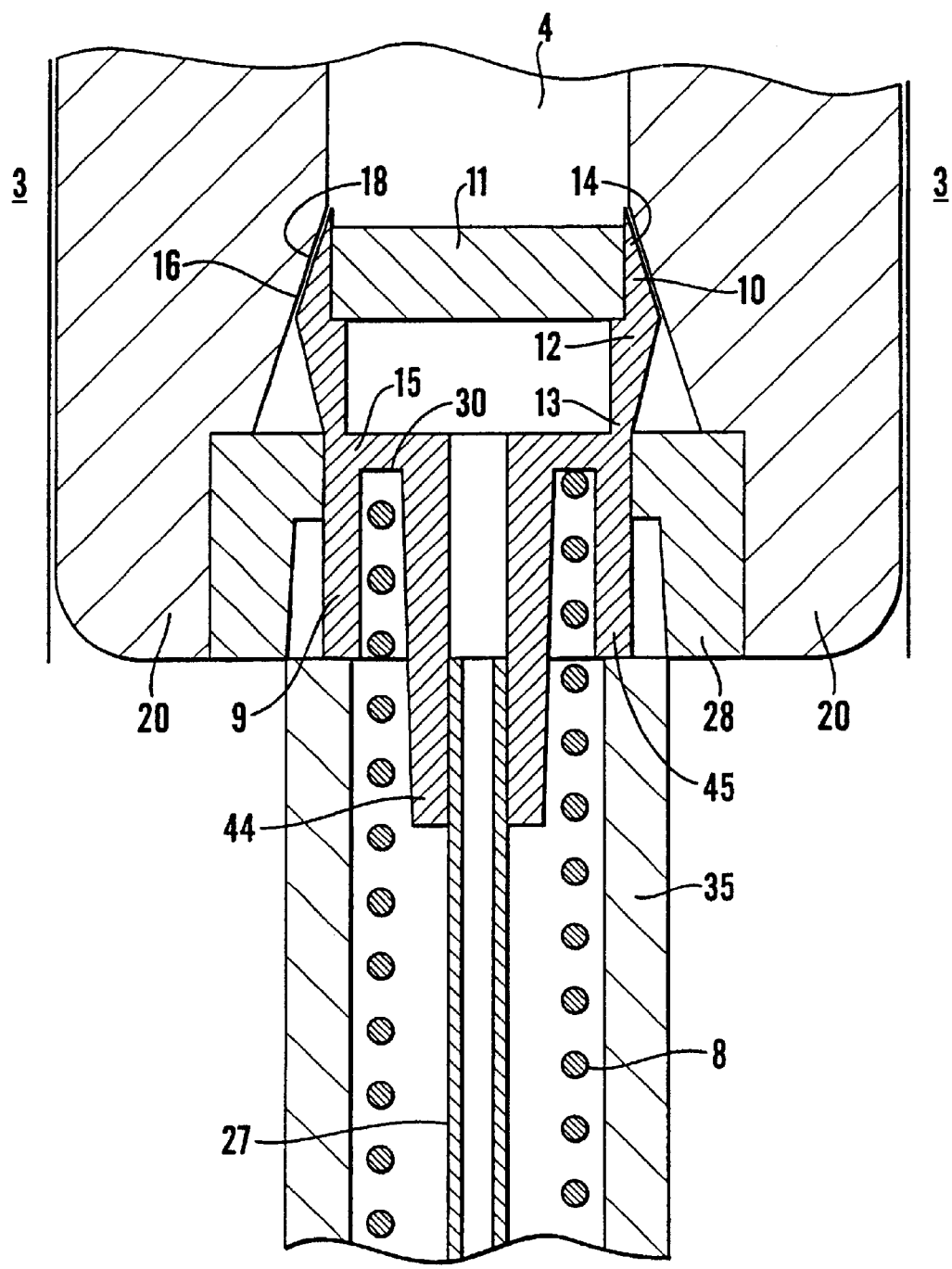
FIG. 7 illustrates the needle retracting mechanisms in FIG. 6 in a larger scale.

FIG. 7 illustrates the needle retracting mechanism in FIG. 6 in a larger scale. The retainer 9 has a design which differs from the previously illustrated retainer designs. The elastic arms 12 have a more slender design than in FIG. 2, but functions similarly. The compressible portion 10 of the retainer 9, i.e. the second ends 14 of the elastic arms 12, are in a retaining position. Holding sides 42, see FIG. 2, is not included in the retracting mechanism in FIG. 7. The retainer base portion 15 has an inner projection 44 and an outer projection 45, which between them form the abutting portion 30 for the actuator 8. The outer retainer projection 45 abuts an actuator holder portion 35 of the body 3, and the retainer 9 is thus prevented from moving in the direction of the second end 6 of the body 3. Further FIG. 7 illustrates a retainer holder 28, which holds and centres the retainer 9 relative to the sleeve 20. A contact between an injectant and the spacer 11 causes the spacer to deform or break, which causes an automatic release of the actuator 8 and the subsequent retraction of the retainer 9 and the needle 27 into the needle retraction chamber 4, as discussed above.

The position of the body 3 relative to the sleeve 20 which is illustrated in FIGS. 6 and 7 is designated the operating position, i.e. the needle 27 is operable and the syringe can be used for injection.

The body 3, see FIG. 6, has a body lug 37 which is slideable in a sleeve track 38 on the outside of the sleeve 20. The sleeve track 38 is terminated in a sleeve lug 36, which is slideable in a body track 39 on the inside of the body 3. The sleeve 20 is thereby movable relative to the body 3.

Figure 8:
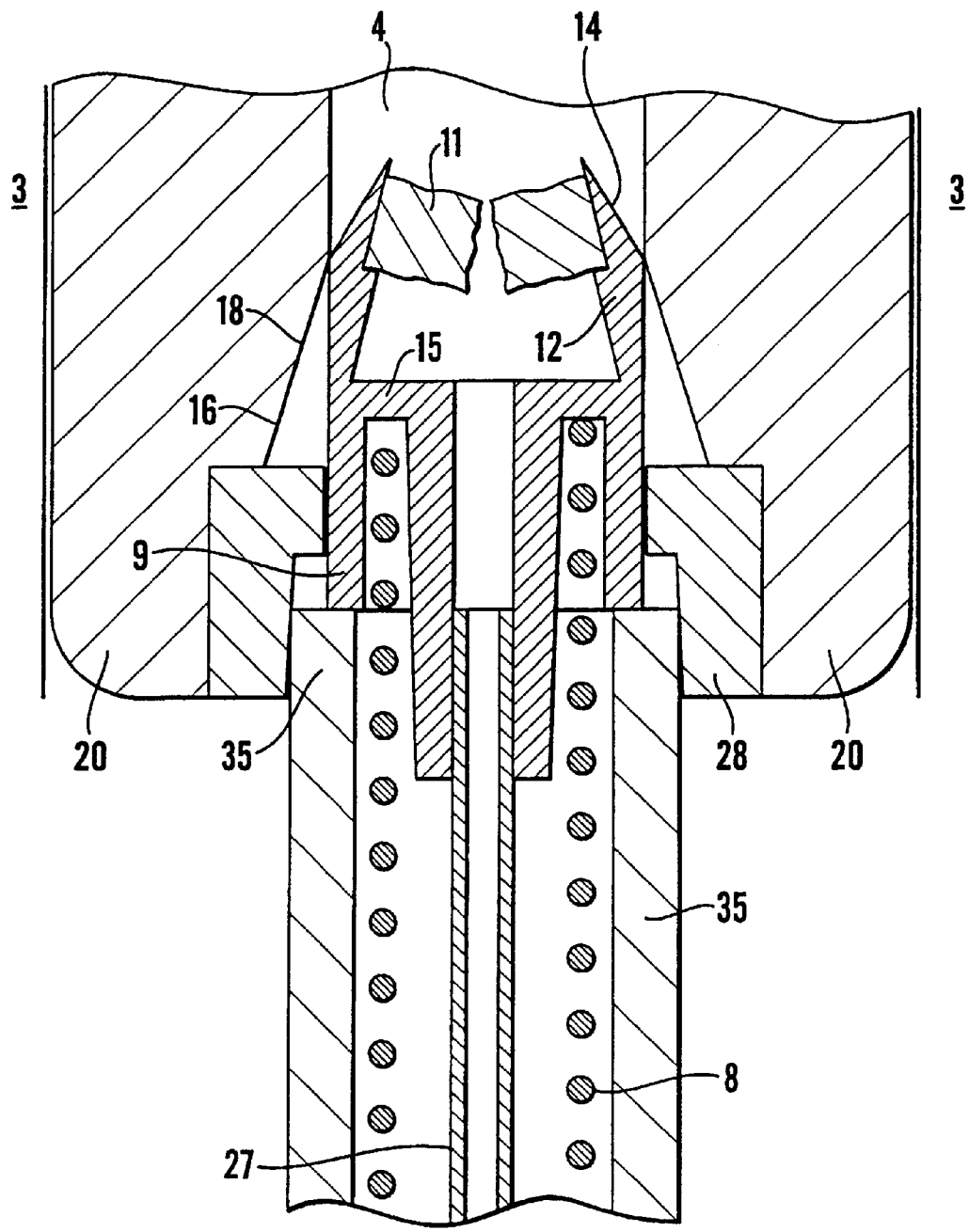
FIG. 8 illustrates the needle retracting mechanisms in FIG. 7 with the retainer in a release position caused by a manual release.

FIG. 8 illustrates the needle retracting mechanisms in FIG. 7 after the sleeve 20 has been moved towards the retainer 9. The retainer 9 is kept in place by the actuator holder 35, while the retainer holder 28 has moved down on the outside of the actuator holder 35. The movement of the sleeve 20 causes the funnel-shaped sides 16 of the entrance opening 18 to press the second ends 14 of the elastic arms 12 towards the release position. This causes an increase in the forces between the elastic arms 12 and the spacer 11, which causes the spacer 11 to deform or break. The funnel-shaped sides 16 and/or the actuator 8 are thereby free to force the second ends 14 of the elastic arms completely into the release position, as illustrated in FIG. 8. In this position the actuator 8 is free to release, and the actuator therefore expands and forces the retainer 9 with the needle 27 through the entrance opening 18 and into the needle retraction chamber 4. A manual needle retraction is thereby carried out.

Figure 9:
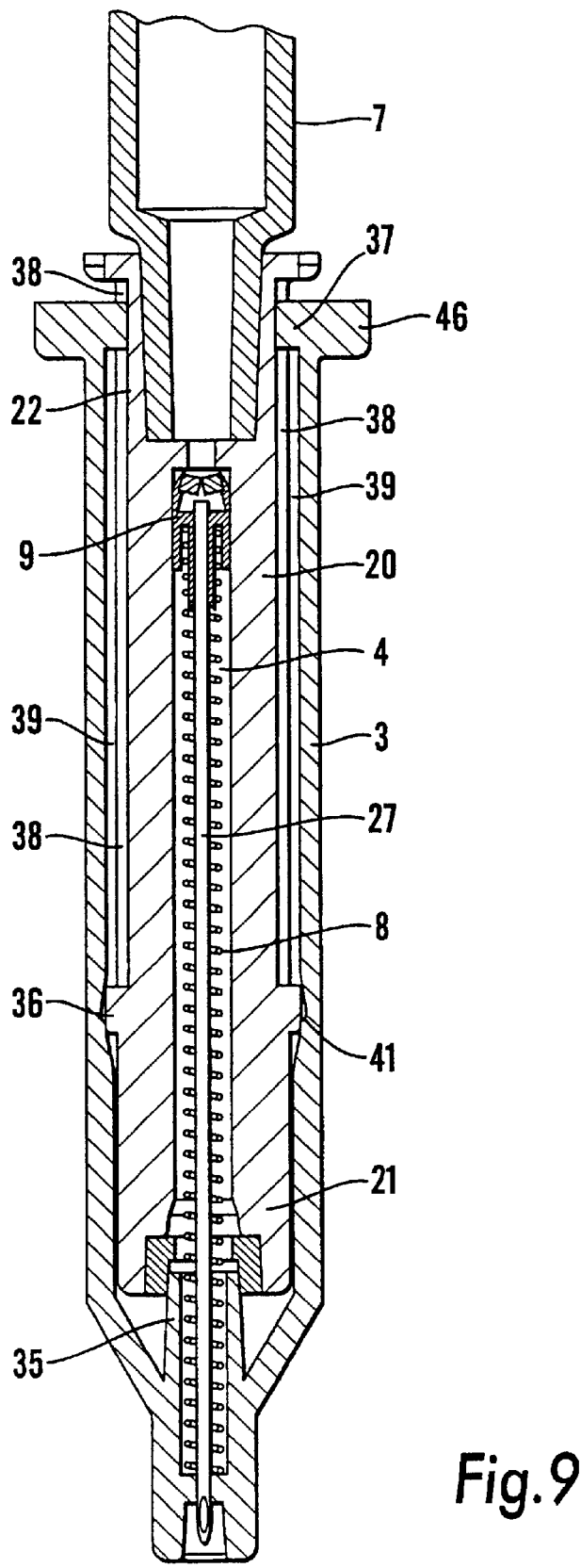
FIG. 9 illustrates the needle holder in FIG. 6 after manual release.

FIG. 9 illustrates the needle holder in FIG. 6 after manual retraction of the retainer 9 and needle 27. This position of the body 3 relative to the sleeve 20 is designated the retracted position.

The movement of the body from the operating position to the retracted position should not take place unintentionally, and the sleeve 20 and the body 3 therefor have yieldable fixation means for fixing the body 3 in the operating position. This yieldable fixation means is formed by the sleeve lugs 36, which in the operating position of the sleeve (see FIG. 6) abuts the ends 41 of the body tracks 39. Both the sleeve and the body are made from plastic, which is a yieldable material. A movement of the body 3 towards the barrel, i.e. the body 3 is "retracted", while the sleeve 20 is kept in place, causes the sleeve lugs 36 and the ends 41 of the body tracks 39 to yield, and the body 3 ends up in the retracted position, as illustrated in FIG. 9. This "retracting" of the body is carried out by the user by pulling a body flange 46 towards the barrel 7, while keeping the sleeve 20 in place by the outlet 19 of the syringe 2.

Figure 10:
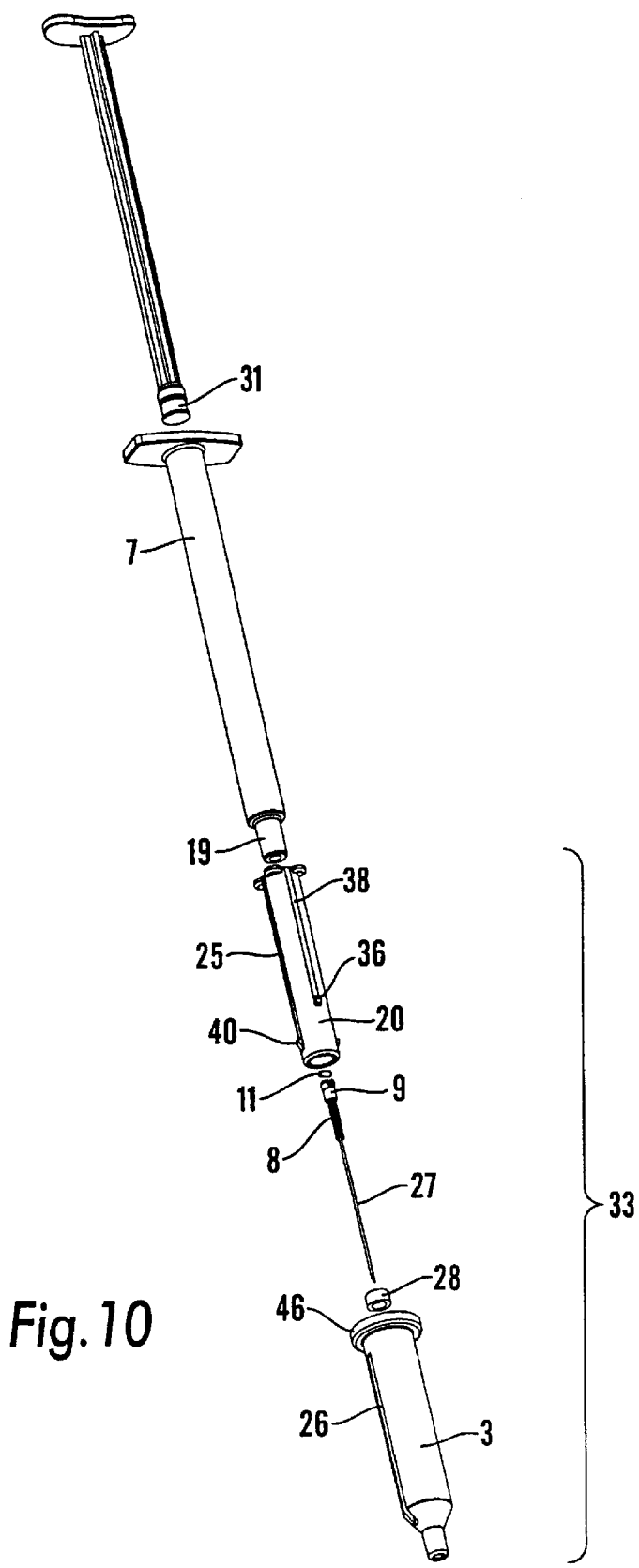
FIG. 10 is an exploded view of a syringe with a needle holder with both an automatic and a manual needle retracting mechanism according to the invention.

FIG. 10 is an exploded view of a syringe with a plunger 31 and a barrel 7, and a needle holder 33 with both an automatic and a manual needle retracting mechanism according to the invention. In addition to the items discussed above, which shall not be repeated, FIG. 10 also illustrates a sleeve ridge 25 and a corresponding body slot 26. These items are for guiding the relative movement of the body and sleeve. A guiding lug 40 is located in the end of the sleeve ridge 25, to prevent the sleeve 20 from being withdrawn from the body 3.

Figure 11:
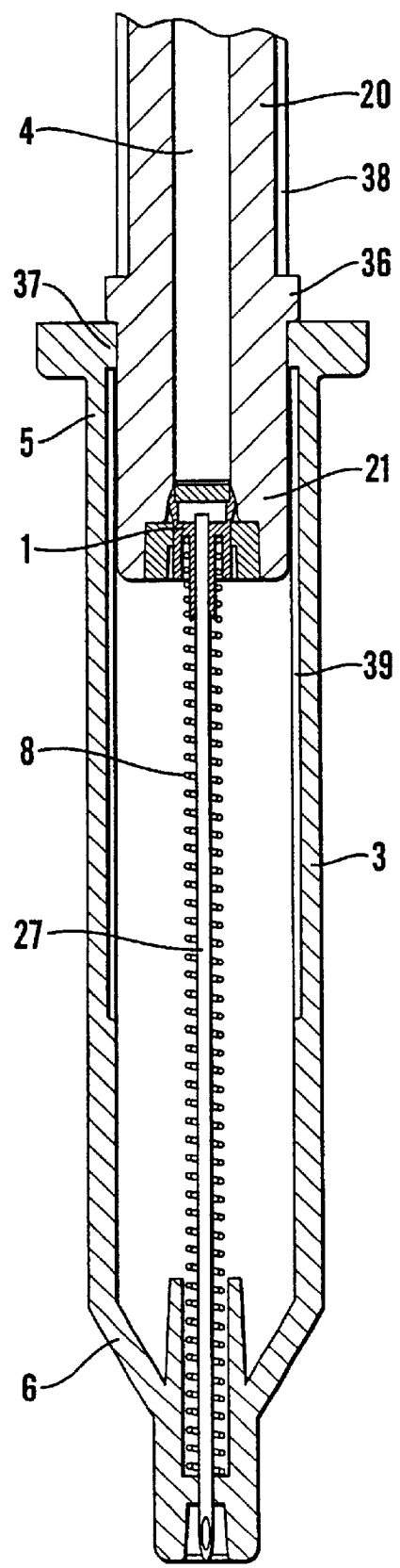
FIG. 11 illustrates the needle holder in FIG. 6 in an extended position.

FIG. 11 illustrates the needle holder in FIG. 6 in a position designated the extended position, in which the body 3 have been "extended" over the needle 27. The body 3 has been slid relative to the sleeve 20 to a position in which the sleeve lugs 36 are on the outside of the body, and abut the body lugs 37. The body lugs 37 have been compressed in radial direction, and hold the sleeve firmly. The guiding lugs 40

(see FIG. 10) prevent a further relative movement of the body and the sleeve.

The extended position is a storage position, in which the needle retracting mechanism 1 is located in the first end 5 of the body 3, the actuator 8 is relieved and the needle 27 is drawn into the body 3. The abutting lugs 36 and 37 form yieldable fixation means for fixing the body 3 in the extended position, which ensures that a certain minimum force is required to move the body 3 into the operating position, in order to prevent that the needle holder unintentionally is prepared for use.

Prior to use, a user holds the sleeve 20 in place by the outlet of the syringe barrel, and forces the body 3 towards the operating position by pulling the body flange 46 towards the syringe barrel, which causes the lugs 36 and 37 to yield. He further slides the body 3 into the operating position, in which the retainer 9 is located in the second end 6 of the body 3, the actuator 8 is pretensioned and the needle 27 is operable.

Figure 6A:
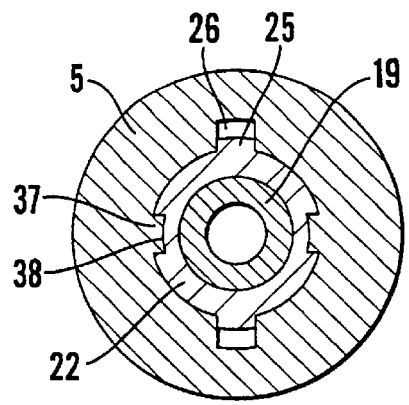
FIGS. 6a–c are cross-sections, taken along lines VIa—VIa, VIb—VIb and VIc—VIc in FIG. 6, respectively.
Figure 6B:
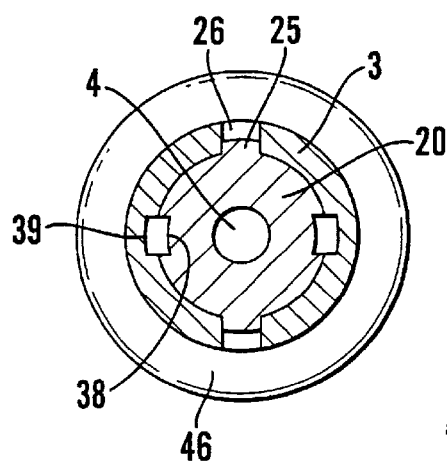
Figure 6C:
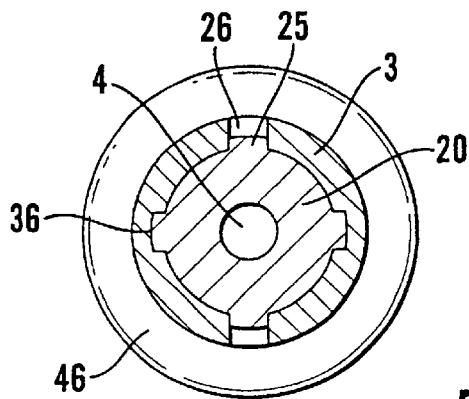

For a further understanding of the arrangement of the sleeve ridges 25, body slots 26, sleeve lugs 36, body lugs 37, sleeve tracks 38 and body tracks 39, reference is made to FIG. 6a, 6b and 6c, which are cross-sections, taken along lines VIa—VIa, VIb—VIb and VIc—VIc in FIG. 6, respectively. It should be understood that other guiding arrangements to fulfil the same purpose as these items are conceivable.

Figure 12:
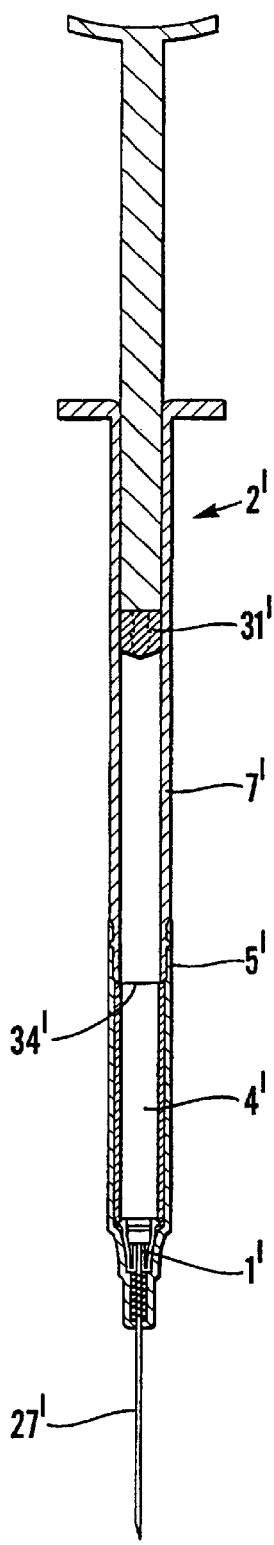
FIG. 12 illustrates a hypodermic syringe with an automatic and a manual needle retracting mechanism according to the invention, in a retaining position.

FIG. 12 illustrates a hypodermic syringe 2' according to the invention, in which an automatic and a manual needle retracting mechanism is integrated in the syringe.

Figure 13:
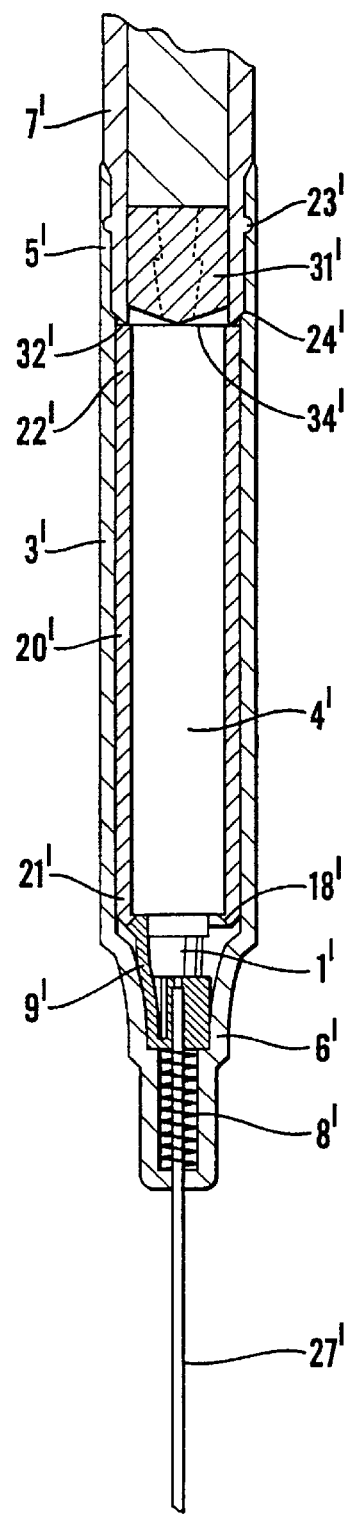
FIG. 13 illustrates the needle retracting mechanisms in FIG. 12 in a larger scale.

FIG. 13 illustrates the needle retracting mechanism in FIG. 12 in a larger scale.

The syringe 2' comprises a barrel 7', a plunger 31', and a needle retracting mechanism 1' with a retainer 9' of the type which is illustrated in FIG. 5. The needle retracting mechanism 1' is housed in a second end 6' of a body 3', and is illustrated in a retaining position. A first end 5' of the body 3' forms an extension of the barrel 7', and is fixed to the barrel 7' by a barrel collar 23' which engages a corresponding groove in the body 3'. Further a step 24' on the inside of the body 3' abuts the end of the barrel 7'. A sleeve 20' is housed in the body 3' and forms a needle retraction chamber 4'. The end 21' of the sleeve 20' proximal to the retainer 9' has a funnel-shaped entrance opening 18', while the end 22' of the sleeve 20' distal to the retainer 9' forms an abutment 32' for the plunger 31' when the plunger 31' is close to the bottom 34' of the barrel 7'. A further movement of the plunger 31' into the barrel 7' forces the sleeve 20' towards the retainer 9', which causes the release of the actuator 8' and the retraction of the needle 27', as discussed above.

It should be understood that an omission of the sleeve 20', and a design of the body 3' similar to the body 3 in FIGS. 1–3 in the area of the retainer 9', would create a syringe with an automatic needle retracting mechanism only, which may be preferable due to lower production cost.

The essential parts of the mechanism, the needle holder and the syringe according to the invention can be produced from plastic by moulding. Typical plastics include polycarbonate, acetal, polyoxymethylene, polypropylene and polyamide.

The material of the spacer has been discussed above. The needle can be a conventional steel needle, which may be fixed to the retainer by a tight fitting.

The illustrated actuator is a helical compression spring which is made from steel.

The inventive automatic needle retracting mechanism and the preferred embodiment comprising the possibility of manual needle retracting, can thus be realised both in a separate needle holder, which has the advantage that it can be used with a wide range of syringes available on the market, and a purpose designed syringe which has the advantage that no fitting of a separate needle holder is required prior to use, and that a re-use of the syringe by exchanging the needle holder is prevented.

Although the invention is described by means of special embodiments, the scope of the invention as stated in the patent claims is not to be considered in any way restricted to these embodiments.

What is claimed is:

1. A needle retracting mechanism (1) for a hypodermic syringe (2), comprising a body (3) with a needle retraction chamber (4), which body (3) in a first end (5) is adapted to receive injectant from a syringe barrel (7) and in a second end (6) slidingly supports a needle (27) which by means of a force from a pretensioned actuator (8) is retractable into the needle retraction chamber (4), the actuator (8) being releasable by response to the injectant, characterised in comprising
    a funnel-shaped entrance opening (18) to the needle retraction chamber (4),
    a retainer (9) for the actuator (8) and the needle (27), the retainer (9) comprises a compressible portion (10) which in a retaining position is bigger than the entrance opening (18) and abuts funnel-shaped sides (16) of the entrance opening (18), and in a compressed release position is smaller than the entrance opening (18) and can enter the needle retraction chamber (4) together with the needle (27), the pretensioned actuator (8) forces the retainer (9) into the funnel-shaped entrance opening (18), forcing the compressible portion (10) towards the release position,
    a spacer (11) for keeping the compressible portion (10) in the retaining position, made from a material which after some time in contact with the injectant loses its mechanical strength,
    whereupon a contact between the spacer (11) and the injectant causes the spacer (11) to lose its mechanical strength, the actuator (8) forces the compressible portion (10) into the release position and into the entrance opening (18), causing the retainer (9) and needle (27) to enter the needle retraction chamber (4).

2. A needle retracting mechanism (1) according to claim 1, characterised in that the compressible portion (10) of the retainer (9) comprises elastic arms (12) which in first ends (13) are integral with a base portion (15) of the retainer (9) and in second ends (14) are moveable between the retaining position and the release position.

3. A needle retracting mechanism (1) according to claim 2, characterised in that the second ends (14) of the elastic arms (12) have oblique end faces (17), corresponding to the funnel-shaped sides (16) of the entrance opening (18).

4. A needle retracting mechanism (1) according to claim 2, characterised in that the elastic arms (12) have mountings (29) for the spacer (11).

5. A needle retracting mechanism (1) according to claim 2, characterised by two arms (12) and a spacer (11) formed by a bolt (11) which is mounted between the arms (12).

6. A needle retracting mechanism (1) according to claim 2, characterised by three arms (12) and a spacer formed by a ring (11') which is mounted between the arms (12).

7. A needle retracting mechanism (1) according to claim 1, characterised in that the needle (27) is fixed to the retainer (9).

8. A needle retracting mechanism (1) according to claim 1, characterised in that the retainer (9) comprises an abutting portion (30) for the actuator (8).

9. A needle retracting mechanism (1) according to claim 1, characterised in that the spacer (11) is made from alginate.

10. A needle retracting mechanism (1) according to claim 1, characterised in that the spacer (11) is made from a water soluble polymer.

11. A needle retracting mechanism according to claim 1, characterised in comprising an inner sleeve (20) which forms the needle retraction chamber (4) and in an end (21) proximal to the retainer (9) is provided with said funnel-shaped entrance opening (18), the sleeve (20) being movable relative to the body (3), towards the retainer (9), an abutment (35) for the retainer (9) in the second end (6) of the body (3), whereupon a movement of the sleeve (20) towards the retainer (9) causes the funnel-shaped sides (16) of the entrance opening (18) to press the compressible portion (10) of the retainer (9) towards the release position and deform the spacer (11), whereupon the funnel-shaped sides (16) and/or the actuator (8) forces the compressible portion (10) into the release position and into the entrance opening (18), causing the needle (27) to enter the needle retraction chamber (4) by the force of the actuator (8).

12. A needle holder (33) for a hypodermic syringe (2), characterised in comprising a needle retracting mechanism (1) according to claim 11, in which the end (22) of the sleeve (20) distal to the retainer (9) is adapted to match an outlet (19) from a syringe barrel (7), and the body (3) is slideable on the sleeve (20) from an operating position in which the compressible portion (10) of the retainer (9) is in the retaining position and the needle (27) is operable, to a retracted position in which the sleeve (20) is moved towards the retainer (9), causing the release of the actuator (8) and the retraction of the needle (27).

13. A needle holder (33) according to claim 12, characterised by the sleeve (20) and/or the body (3) having yieldable fixation means (36, 41) for fixing the body (3) in the operating position.

14. A needle holder (33) according to claim 12, characterised in that the body (3) is slideable on the sleeve (20) from an extended position in which the retainer (9) is located in the first end (5) of the body (3), the actuator (8) is relieved and the needle (27) is drawn into the body (3), to the operating position in which the retainer (9) is located in the second end (6) of the body (3), the actuator (8) is pretensioned and the needle (27) is operable.

15. A needle holder (33) according to claim 14, characterised by the sleeve (20) and/or the body (3) having yieldable fixation means (36, 37) for fixing the body (3) in the extended position.

16. A needle holder (33) according to claim 12, characterised in that the sleeve (20) and the body (3) are provided with corresponding ridges (25) and slots (26) for guiding the movement of the body (3) on the sleeve (20).

17. A hypodermic syringe (2') comprising a barrel (7') and a plunger (31'), characterised in comprising a needle retracting mechanism (1') according to claim 11, in which the first end (5') of the body (3') forms an extension of the barrel (7'), and the end (22') of the sleeve (20') distal to the retainer (9') forms an abutment (32') for the plunger (31') when the plunger (31') is close to the bottom (34') of the barrel (7'), causing a further movement of the plunger (31') into the barrel (7') to force the sleeve (20') towards the retainer (9'), causing the release of the actuator (8') and the retraction of the needle (27').

18. A needle holder (33) for a hypodermic syringe (2), characterised in comprising a needle retracting mechanism (1) according to claim 1, in which the first end (5) of the body (3) is adapted to match an outlet (19) from a syringe barrel (9).

19. A hypodermic syringe (2') comprising a barrel (7') and a plunger (31'), a needle retracting mechanism (1') according to claim 1, in which the first end (5') of the body (3') forms an extension of the barrel (7').

\* \* \* \* \*